US 6,566,556 B2

(12) United States Patent
Tsuneki et al.

(10) Patent No.: US 6,566,556 B2
(45) Date of Patent: May 20, 2003

(54) METHOD FOR PRODUCTION OF ALKANOLAMINE AND APPARATUS THEREFOR

(75) Inventors: Hideaki Tsuneki, Tokyo (JP); Koji Takeda, Yokosuka (JP); Fumiaki Morishita, Tokyo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/999,352

(22) Filed: Nov. 15, 2001

(65) Prior Publication Data

US 2002/0123653 A1 Sep. 5, 2002

(30) Foreign Application Priority Data

Dec. 19, 2000 (JP) .......................... 2000-385145
Sep. 27, 2001 (JP) .......................... 2001-297495
Sep. 27, 2001 (JP) .......................... 2001-297496

(51) Int. Cl.$^7$ ..................... C07C 213/02; C07C 213/04
(52) U.S. Cl. ......................... 564/475; 564/479
(58) Field of Search ................... 564/475, 479

(56) References Cited

U.S. PATENT DOCUMENTS

| | | | | |
|---|---|---|---|---|
| 4,119,670 A | 10/1978 | Tsuchiya | ................ | 260/585 C |
| 4,355,181 A | * 10/1982 | Willis, Jr. et al. | .......... | 564/477 |
| 5,599,999 A | * 2/1997 | Moriya et al. | .............. | 564/477 |
| 6,169,207 B1 | 1/2001 | Tsuneki et al. | ............. | 564/475 |

FOREIGN PATENT DOCUMENTS

| | | | | |
|---|---|---|---|---|
| EP | 0 941 986 A2 | * 9/1999 | ......... | C07C/213/04 |
| EP | 1 043 063 A2 | 10/2000 | .............. | B01J/8/00 |
| EP | 1 104 752 A2 | 6/2001 | ......... | C07C/213/04 |

OTHER PUBLICATIONS

Database WPI Section Ch, Week 200043 Derwent Publications Ltd., London, GB; Class E16, AN 2000–489850 XP002192583 & RU 2 141 475 C (Khimtekh Inzhiniring Stock Co), Nov. 20, 1999, abstract.
Patent Abstracts of Japan vol. 013, No. 419 (C–637), Sep. 18, 1989 & JP 01 157938 A (Mitsubishi Gas Chem Co Inc), Jun. 21, 1989, abstract.

* cited by examiner

*Primary Examiner*—Brian Davis
(74) *Attorney, Agent, or Firm*—Fish & Richardson P.C.

(57) ABSTRACT

A method for producing an alkanolamine from liquid ammonia in the presence of a solid catalyst efficiently with both the cost of equipment and the expense of utility repressed is provided. After not less than 60% of the ammonia has been recovered as liquid ammonia from the product solution, the remaining ammonia is recovered as aqueous ammonia solution through the steps of stripping and absorption in water. Separately, a dialkanolamine can be selectively and efficiently produced by circulating part of the product solution to the reactor.

20 Claims, 8 Drawing Sheets

FIG.1

PRODUCT

FIG.2

PRODUCT

METHOD FOR PRODUCTION OF ALKANOLAMINE AND APPARATUS THEREFOR

BACKGROUND OF THE INVENTION

1. Field of the Invention

This invention relates to a method for the production of an alkanolamine by the reaction of ammonia and an alkylene oxide using a solid catalyst, and an apparatus used therefor.

2. Description of Related Art

A method for producing ethanolamine by causing ethylene oxide ($C_2H_4O$) to react with aqueous ammonia ($NH_3$) solution (with the ammonia concentration in range of 20 to 40% by weight) has been adopted as a means to effect commercial production of alkanolamines. The ethanolamine thus produced is in the form of a mixture of three components, monoethanolamine ($NH_2CH_2CH_2$—OH), diethanolamine [$NH(CH_2CH_2$—$OH)_2$], and triethanolamine [$N(CH_2CH_2$—$OH)_3$]. The method represses the formation of triethanolamine. The reaction, therefore, is generally carried out with the molar ratio of ammonia to ethylene oxide set at a large ammonia excess in the approximate range of 3 to 5:1. In spite of the effort, the selectivity for triethanolamine is in the range of 10 to 20% by weight or more and the selectivity for diethanolamine is not more than 40% by weight.

This method for producing an alkanolamine using aqueous ammonia solution may be referred to as "aqueous ammonia solution method for production of alkanolamine."

Substantially no reaction occurs between the alkylene oxide and ammonia in the system using no aqueous ammonia solution, namely anhydrous system. For this reaction, therefore, a catalyst, such as an ion-exchange resin, molecular sieve, silicia-alumina, acid-activated clay, a catalyst in which a rare earth element is supported on heat-resistant carriers, is indispensable.

U.S. Pat. No. 6,169,207 B1 discloses a catalyst which inhibits the formation of trialkanolamine and permits selective production of dialkanolamine. European Patent Publication Nos. 104363 and 1104752 disclose methods for starting up reactions, methods for packing catalysts, reaction apparatuses, and methods for regenerating catalysts. No mention is made anywhere in these references about a process including a system for recovering unreacted ammonia.

In the production of an alkanolamine by the reaction of liquid ammonia and an alkylene oxide, recovery of unreacted ammonia is required since the reaction uses excess ammonia. In order for this unreacted ammonia to be recovered as liquid ammonia, an ammonia-recovering column must be pressurized. During the application of pressure, the ammonia concentration in the bottom product of the column is increased to a level of about 4 to 20% by weight. From the bottom product, therefore, ammonia cannot be recovered through just one stage of distillation. It is further necessary that the temperature of the bottom product of the column, be held down as low as possible to prevent the alkanolamine from being degraded. The bottom product temperature, for example, must be held down to not more than 300° C., preferably not more than 250° C. The removal of ammonia from the bottom product under such conditions entails decompressing the column. To recover ammonia at the top of the column, it is necessary to lower the temperature to a very low level by the use of a refrigerator or transform the ammonia into liquid ammnonia by compression with a compressor. This entails problems such as increasing the size of the equipment, increasing the construction cost, and incurring much expense.

Meanwhile, when improving the production of alkanolamine, in particular the dialkanolamine, and when a catalyst having high selectivity to dialkanolamine is used, the product contains mainly mono alkanolamines. The selectivity to dialkanolamines is not sufficiently high unless the concentration of alkylene oxides is increased. Incidentally, when the concentration of alkylene oxides is excessively high the reaction heat per unit of the product solution will be inevitably large and the adiabatic reaction will not occur because of an undue rise of temperature. For solving this problem, multistage adiabatic reactions that use a plurality of reactors and that supply divided alkylene oxide may be carried out. This reaction uses liquid ammonia as a raw material at an elevated temperature. Therefore, the reaction needs a plurality of reactors capable of withstanding very high pressure and, as a result, raises the cost of equipment.

SUMMARY OF THE INVENTION

An object of this invention is to solve such problems, and to provide a method for recovering unreacted ammonia using water as an absorbent in the production of alkanolamines without lowering the temperature of the bottom product with a refrigerator or lowering the pressure thereof with a compressor.

According to the first aspect of this invention, it provides a method for producing an alkanolamine by the reaction of liquid ammonia and a corresponding alkylene oxide using a solid catalyst, which method comprises the following steps:

a) recovering not less than 60% by weight of the ammnonia, based on the weight of a product solution which is emerged from the outlet of a reactor and contains unreacted ammonia and alkanolamines, as liquid ammonia and the remainder thereof as a bottom product at an ammonia-recovering column;

b) directing the bottom product to an ammonia-stripping column in which the ammonia is stripped out; and c) feading the stripped ammonia to an ammonia absorption column in which the ammonia is absorbed by means of water, thereby recovering it as aqueous ammonia solution.

According to the present invention, it can produce alkanolamines by the reaction of liquid ammonia and the corresponding alkylene oxide inexpensively and efficiently without expensive devices such as refrigerators and compressors, which are used in the ammonia removal and ammonia recovery from the product solution containing ammonia, e.g., 4 to 20% by weight of ammonia.

Further, we have conducted a diligent study with a view to solving the problems mentioned above, and, as a result, found that by circulating part of the product solution formed in the reactor to the inlet to the reactor, it is possible to obtain an alkanolamine, in particular selectively dialkanolamine, of a required composition by the use of an adiabatic reactor. This invention has been perfected as a result.

According to the second aspect of this invention, it can provide a method for producing an alkanolamine by the reaction of liquid ammonia and a corresponding alkylene oxide effected by the use of a fixed-bed reactor in the presence of a solid catalyst, which method is characterized by having part of the product solution sent to the reactor.

Then, according to the third aspect of this invention, it can provide an apparatus to be used in the production of an alkanolamine by the reaction of liquid ammonia and a corresponding alkylene oxide in the presence of a solid catalyst, which apparatus is characterized by comprising a fixed-bed reactor, a pressure-controlling valve disposed on the downstream side of the reactor, a pump for circulating the product solution to the reactor, a booster pump for supplying the raw material ammonia to the reactor, and a booster pump for supplying the raw material alkylene oxide to the reactor and consequently allowing control of the amount of the product solution to be circulated to the reactor by means of the pump mentioned above.

According to this invention, it is possible to carry out the reaction of an alkylene oxide and liquid ammonia by the use of one reactor and produce a dialkanolamine selectively and efficiently, and it is further possible to provide an apparatus for carrying out this reaction.

The above and other objects, features and advantages of the present invention will become clear from the following description of the preferred embodiments.

BRIEF DESCRIPTION OF DRAWINGS

The accompanying drawing incorporated in and forming a part of the specification, illustrates several aspects of the present invention, and together with the description serve to explain the principles of the invention. In the drawings.

DETAILED DESCRIPTION OF THE PREFERRED EMBODIMENTS

The alkylene oxide to be used as a raw material in this invention is preferably an alkylene oxide represented by the formula (1):

(1)

wherein $R^1$, $R^2$, $R^3$, and $R^4$ independently denote a hydrogen atom, a methyl or ethyl group. Examples of the alkylene oxide may include alkylene oxides that has 2 to 4 carbon atoms such as ethylene oxide and propylene oxide. The alkanolamines corresponding to these raw materials are obtained.

Examples of the alkanolamines may include monoalkanolamines represented by the formula (2):

(2)

wherein $R^1$, $R^2$, $R^3$, and $R^4$ are the same as in the formula (1) above;

dialkanolamines represented by the formula (3):

(3)

wherein $R^1$, $R^2$, $R^3$, and $R^4$ are the same as in the formula (1) above; and trialkanolamines.

Figure 1:
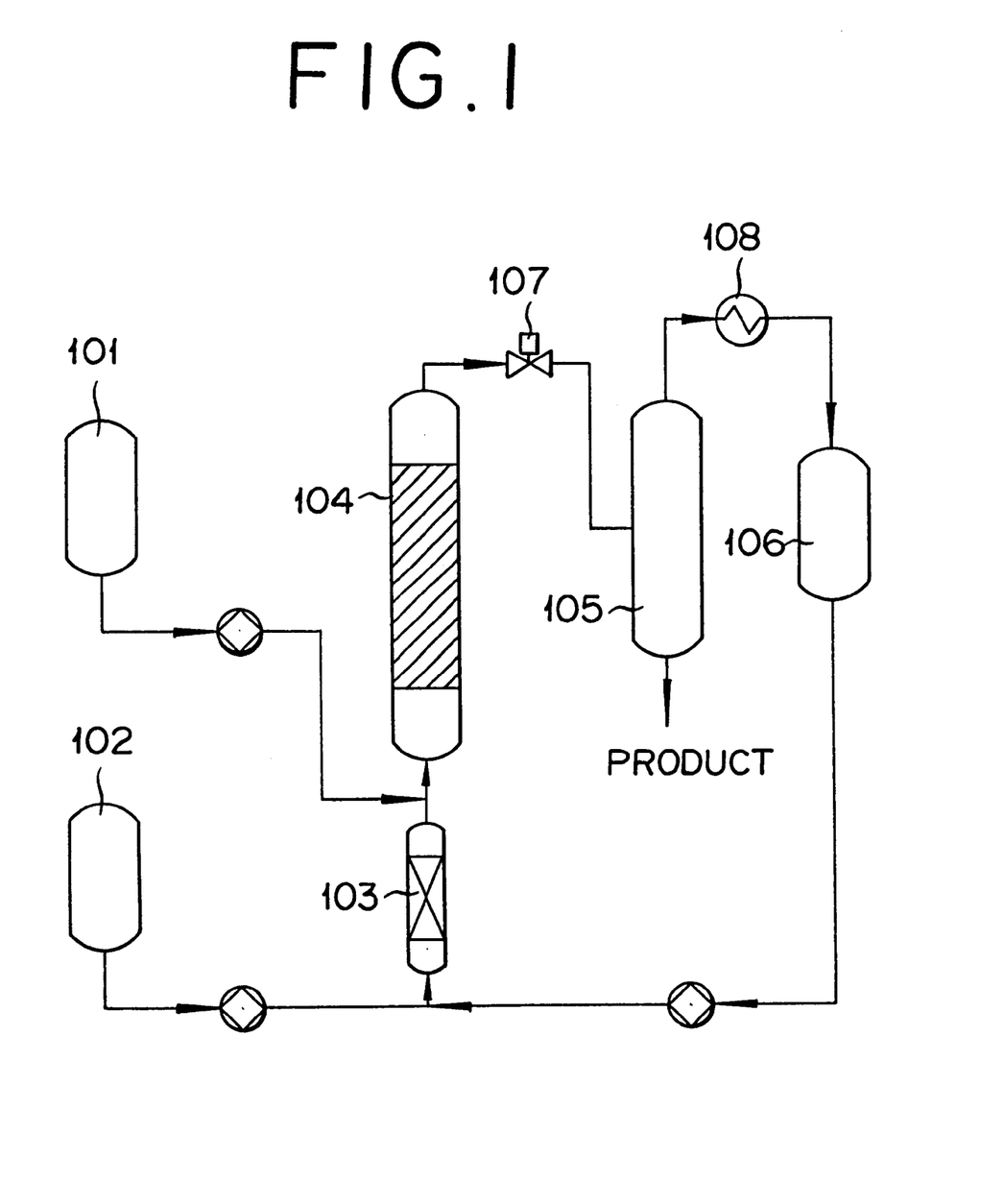
FIG. 1 is a flow sheet schematically illustrating a process for the production of an alkanolamine by the use of a single reactor.

The first aspect of this invention will be described which reaction uses liquid ammonia and an alkylene oxide as raw materials by the use of a pressure type fixed-bed reactor. FIG. 1 is a typical flow sheet illustrating a process for producing an alkanolamine using a reactor not adapted to recycle a product solution produced. In FIG. 1, liquid ammonia is supplied from a liquid ammonia tank 102 via pre-heater 103 to and an alkylene oxide from an alkylene oxide tank 101 to the reactor 104, respectively. Though the rate of the ammonia to be added to the alkylene oxide is not particularly restricted, the amount of ammonia may be in the range of 2 to 30 mols per mol of the alkylene oxide. The pre-heater 103 is aimed at accelerating the heating of the raw materials to the reaction temperature prior to the reaction. The temperature of the pre-heater 103, therefore, is preferred to fall in the range of 20° C. to 100° C. The reaction is adiabatic.

This invention proves effective for selective production of dialkanolamines and, therefore, prefers a catalyst having a high activity and capable of producing the dialkanolamine with a high selectivity. When the reaction uses a solid catalyst, the rate constant of the reaction of the dialkanolamine and an alkylene oxide is defined as $k_3$ and that of the reaction of the monoalkanolamine and the alkylene oxide as $k_2$. The ratio β ($k_3/k_2$) is properly not more than 0.7, preferably not more than 0.5, more preferably not more than 0.4, and still more preferably not more than 0.25. The reaction performed under these conditions is advantageous because it permits selective production of a dialkanolamine with a high efficiency. If the β value exceeds its upper limit, the excess will aggravate selective production of the dialkanolamines since the consecutive reaction from the dialkanolamine to trialkanolamine is too high. It suffices to use a catalyst whose β value is zero for the purpose of completely preventing formation of the trialkanolamines. However, a catalyst whose β value is zero is inconceivable for this reaction since the reaction of an alkanolamine and an alkylene oxide, unlike the reaction of ammonia and an alkylene oxide, proceeds to a certain extent even in the absence of a catalyst.

The incidentaly, the β value can be obtained by the method.

The reaction of ammonia and an alkylene oxide is a consecutive reaction. For the purpose of selectively forming the dialkanolamine as an intermediate product, the catalyst therefore is required to have high selectivity. Specifically, in the reaction, for example, the following three reactions consecutively occur:

$$NH_3 + AO \rightarrow MAA \quad (1)$$

$$MAA + AO \rightarrow DAA \quad (2)$$

$$DAA + AO \rightarrow TAA \quad (3)$$

wherein AO denotes an alkylene oxide, MAA a monoalkanolamine, DAA a dialkanolamine, and TAA a trialkanolamine.

Let us presume that the reactions of (1), (2), and (3) are first order with respect to the concentrations of the raw materials, alkylene oxide, ammonia, and amine and let $k_1$, $k_2$, and $k_3$ stand for the rate constants of the reactions, and the relevant reaction rates will be expressed as follows:

$$r_1 = k_1 C_{NH3} C_{AO} \quad (4)$$

$$r_2 = k_2 C_{MMA} C_{AO} \quad (5)$$

$$r_3 = k_3 C_{DAA} C_{AO} \quad (6).$$

Here, the expression, $\alpha = k_1/k_2$, is defined. Let x, y, z, and u stand respectively for the mol fractions of ammonia, MAA, DAA, and TAA in the product solution in the case of AO conversion being 100%, and the $\alpha$ and $\beta$ will be found from the integration of the reaction formulas (4) to (6) and the weight balance formula, x+y+Z+u=1, to be the solutions of the following nonlinear equations (i) and (ii). These nonlinear equations can be solved by the ordinary method of numerical solution to find the value of $\beta$:

$$y = \frac{x^{\frac{1}{\alpha}} - x}{1 - \frac{1}{\alpha}} \quad (i)$$

$$z = \frac{\alpha}{\alpha - 1}\left(\frac{x - x^{\frac{\beta}{\alpha}}}{\alpha - \beta} - \frac{x^{\frac{1}{\alpha}} - x^{\frac{\beta}{\alpha}}}{1 - \beta}\right) \quad (ii)$$

The solid catalyst whose $\beta$ is not more than 0.7 is for example a microporous material having an effective pore diameter in the range of from 0.45 nm to 0.8 nm, more preferably a catalyst obtained by subjecting such a microporous material to ion-exchange and/or surface treatment with a rare earth element. The range of effective micropore diameter mentioned above is advantageous in that the raw materials for the reaction freely diffuse in the pores without lowering their activities, and the pores allow no trialkanolamine to occur therein, thereby the selectivity to the dialkanolamine is not decreased. Examples of appropriate microporous materials may include MFI type aluminosilicate (so-called ZSM-5), MFI type ferrisilicate, MEL type aluminosilicate (so-called ZSM-11), and BEA. As rare earth elements for the ion-exchange, yttrium, lanthanum, cerium, praseodymium, neodymium, samarium, terbium, ytterbium, or mixtures thereof is used. Among them, yttrium, lanthanum, and cerium prove particularly advantageous. The X and Y type zeolites that have large cavities rarely reveal the shape selectivity expectable from the pore diameters at the outlets and inlets of pores because their cavities are capable of forming large molecules. Further, the outer surfaces of the primary crystal particles are preferred to undergo an outer surface treatment since the shape selectivity cannot be expected of the reaction outside the pores. For examples of the outer surface treatment, a steaming treatment at an elevated temperature, a treatment with silicon tetrachloride, and a treatment with alkoxy silane may be cited.

Specifically, the metallosilicate can be prepared generally by the so-called hydrothermal synthesis method which comprises dispersing a silica source, a metal source, and a structure directing agent in water and heating the resultant aqueous solution in an autoclave and the so-called dry gel method which comprises concentrating a silica source, a metal source, and a structure directing agent until dryness and exposing the produced gel to steam in an autoclave. Further, ZSM-5 and BEA are commercially available. Generally, the ion-exchange site in the microporous material formed by the hydrothermal synthesis contains an alkali metal ion as a counter ion. Such alkali metal ions can be exchanged to the proton type by the ion change with $NH_4^+$ ion and then calcined at an elevated temperature since the state has low activity. Optionally, the tentative ion-exchange with $NH_4^+$ ion may be followed by another round of ion-exchange with a polyvalent cation. Particularly, the ion-exchange with a rare earth element proves favorable because it often results in improving activity and selectivity.

The catalyst is preferably formed in a given shape for a commercial scale. The catalyst is not particularly discriminated, but may include spheres, cylinders, and hollow cylinders. Microporous materials such as metallosilicate are formed of very fine crystals and, in an isolated state, are unusually deficient in formability. In order for the catalyst to be formed, the catalyst is preferred to use a forming auxiliary or a binder. Examples of the forming auxiliary or binder may include various oxide sols such as silica sol, alumina sol, and zirconia sol and clayish minerals. Smectite and kaolin type clayish minerals prove particularly favorable in the aspect of improvement of the formability. When the forming auxiliary is used, though the amount thereof is not particularly limited but only required to permit production of a catalyst aimed at. It is generally not more than 50 weight parts, preferably not more than 40 weight parts, based on 100 weight parts of the microporous material. The catalyst that has grown to a certain extent is preferred to enlarge the pore volume thereof so as to prevent the catalyst from degrading the activity and selectivity thereof. This increase of the pore volume is preferably effected by causing a pore forming agent incorporated into the catalyst prior to the formation followed by a calcination treatment to remove the agent. Examples of the pore forming agent may include various ammonium salts such as ammonium nitrate and ammonium acetate, organic compounds such as oxalic acid, urea, and water-insoluble organic compounds such as various polymers and fibers. The water-insoluble organic compounds are advantageously usable in terms of the efficiency of formation of pores and the ease of formation. Such compounds are required to exhibit hygroscopicity of a certain degree, form fine powders, and permit removal by combustion by a treatment at an elevated temperature of the order of several hundred degrees on the centigrade scale. Particularly crystalline cellulose proves favorable in terms of the ease of handling. As the crystalline cellulose, filter paper, ground powder, and the powder obtained by grinding pulp may be used. When the organic pore-forming agent such as crystalline cellulose is used, it is removed by combustion in the gas of nitrogen, helium, or carbon dioxide that contains oxygen (air is used conveniently) since this agent cannot be decomposed by a simple heat treatment.

Preferably, the reaction temperature is in the approximate range of normal temperature to 200° C. and the reaction pressure in the approximate range of 8 to 15 MPa. Then, LHSV (liquid hourly space velocity) generally falls in the range of 0.5 to 100 hr$^{-1}$, depending on the reaction temperature, the kind of catalyst, and the amount of catalyst used.

The reactor is a fixed-bed reactor, which generally feeds the raw materials and reaction liquid in an upflow current. It is preferred to be an adiabatic type reactor from the viewpoint of the efficiency of reaction.

The reaction product emerged from the reactor 104 is forwarded via a pressure-controlling valve 107 to an ammonia-recovering or ammonia-flushing column 105. In the ammonia-recovering column 105, the ammonia is guided from the top of the column to a condenser 108 and recovered as liquid ammonia in a tank 106 and, at the same time, a mixture of ammonia and alkanolamines is obtained as the bottom product. At this recovery step, 60 to 98% by weight, preferably 70 to 96% by weight, and preferably 80 to 95% by weight, of the ammonia contained in the product solution is recovered as liquid ammonia in the tank 106. If the recovery percentage of ammonia is low, the amount of ammonia to be subsequently recovered in the ammonia-recovering system will increase and the aqueous ammonia solution will be generated in a large amount. This aqueous ammonia solution raises no problem so long as a use is found for the solution. When the aqueous ammonia solution is used as a raw material for the production of alkanolamines by the conventional aqueous ammonia solution method, which will be described below, it is commendable to recover this ammonia to the fullest extent because generation of more aqueous ammonia solution than proportionate to the amount of product is unfavorable. By recovering 60 to 98% by weight of the liquid ammonia, it is possible to attain the effect of enabling the amount of ammonia, which forms the aqueous ammonia solution at the step of recovering the ammonia contained in the product solution produced, to serve the aqueous ammonia solution just enough as, i.e. a raw material for the production of alkanolamines by the aqueous ammonia solution method. Generally, the operating pressure of the ammonia-recovering column 105 may be in the range of 1 to 3 MPa since the cooling water at normal temperature is used as the coolant in the condenser 108. The ammonia-recovering column 105 may contain ammonia at a concentration of 4 to 20% by weight as the bottom product.

Figure 2:
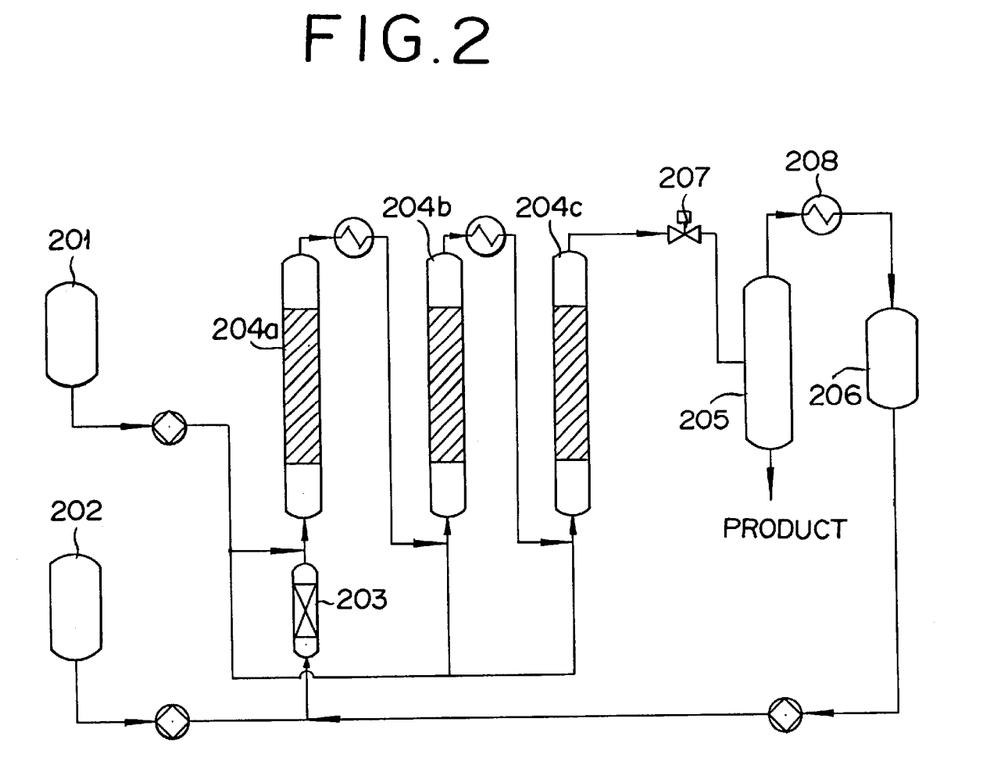
FIG. 2 is a flow sheet schematically illustrating a process for the production of an alkanolamine by the use of three reactors.

FIG. 2 illustrates a typical flow sheet of the process for producing alkanolamines in the case of adopting a plurality of reactors and supplying an alkylene oxide as divided. In FIG. 2, the reference numerals that result from adding 100 to the reference numerals of FIG. 1 denote the same parts as in FIG. 1 unless otherwise specified. This process is capable of heightening the ratio of alkylene oxide/ammonia and increasing the products of dialkanolamines as compared with the process illustrated in FIG. 1. The division ratio of the alkylene oxide can be properly selected based on the ratio of the product aimed at, but may be, for example, 1:1:1 by weight. Part of the product solution produced may be recycled to the reactor. When the catalyst used excels in selectivity for dialkanolamines, the dialkanolamines produced can be increased in amount by recycling the product solution even if only a reactor is used. The method illustrated in FIG. 1 can be similarly adopted here except for the particulars mentioned above.

Now, the second aspect of this invention will be described below. There are two methods for the operation for circulating part of the product solution to the reactor.

Figure 3:
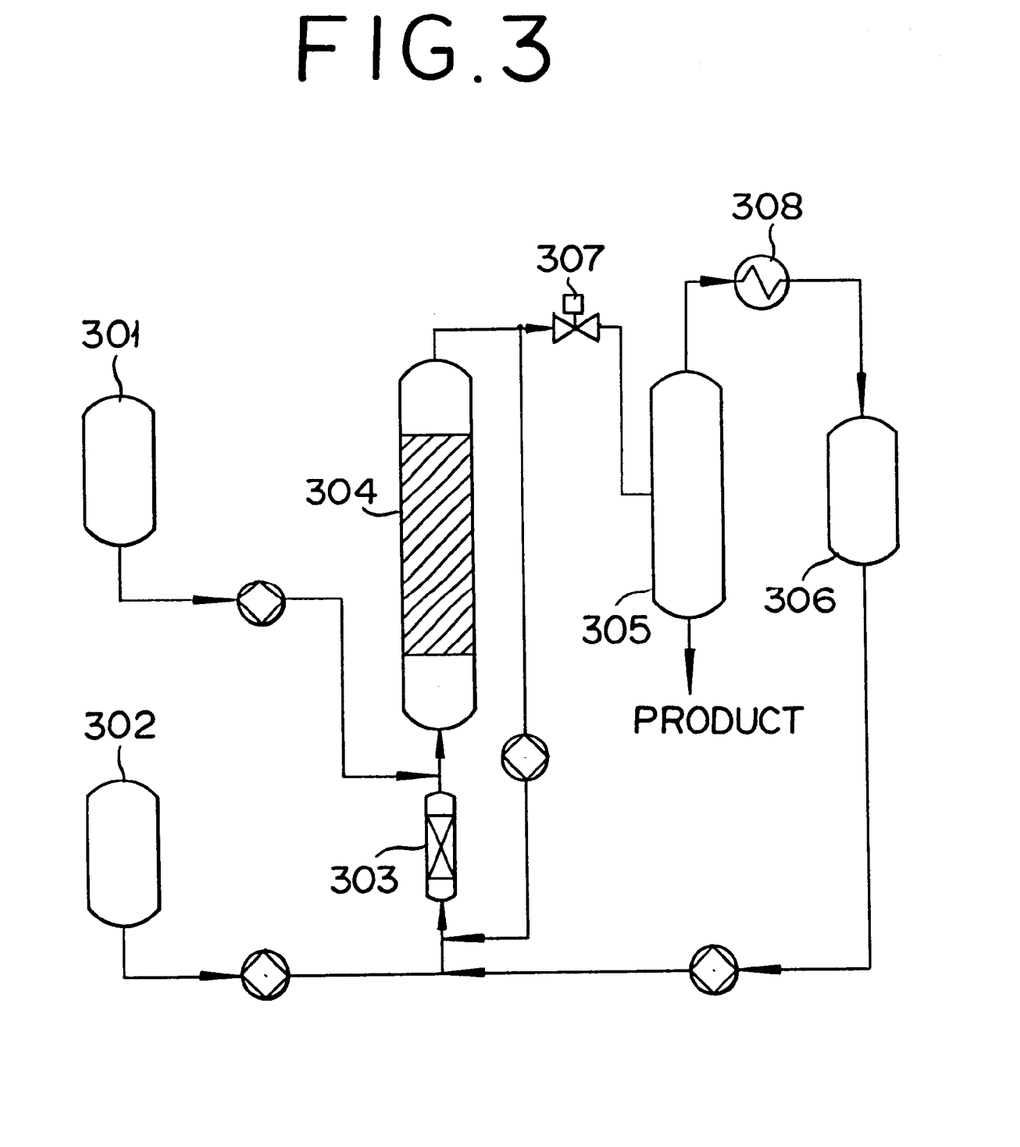
FIG. 3 is a flow sheet schematically illustrating a process for the production of an alkanolamine by the use of a single reactor adapted to recycle the product solution formed therein to the reactor.

The first method, as illustrated in FIG. 3, consists in branching the flow path in front of an ammonia-flashing column and circulating part of the product solution exiting from the reactor to the reactor, with the composition of the product solution kept intact after departure from the outlet of the reactor.

Figure 4:
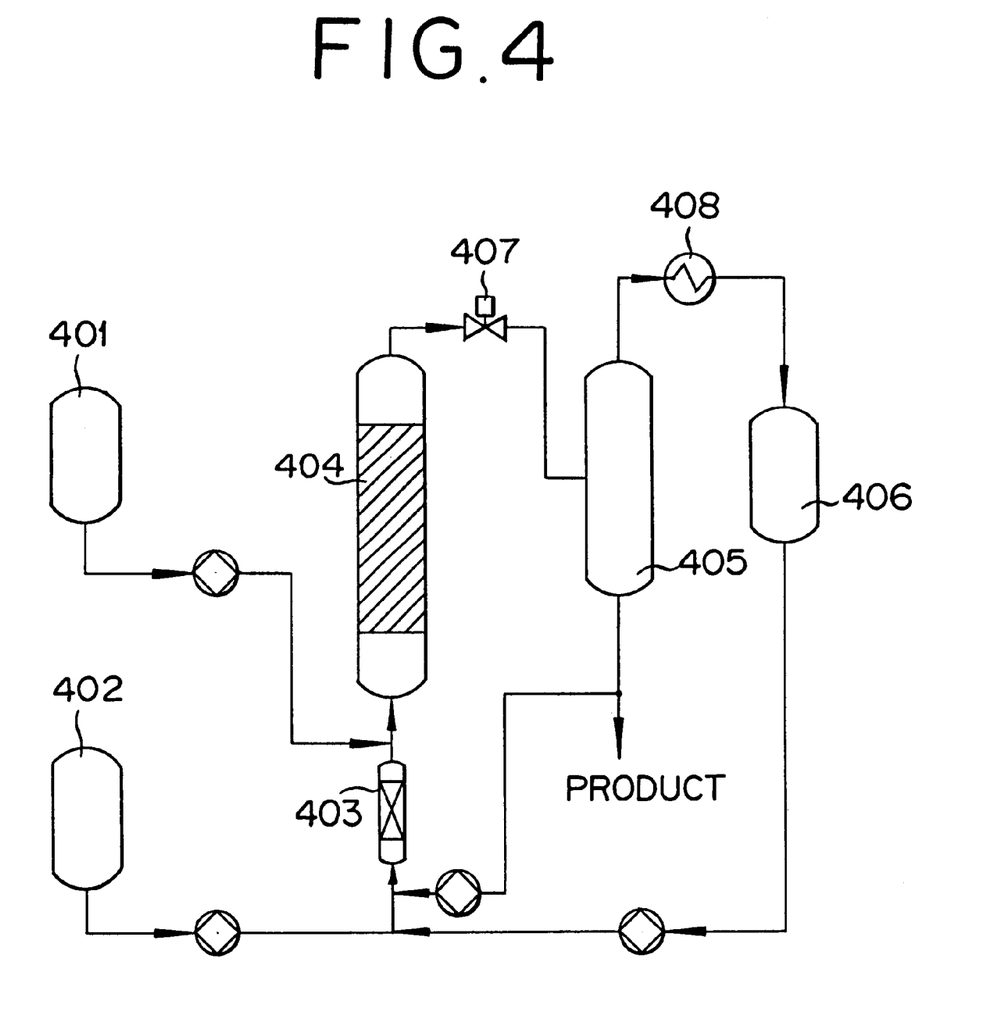
FIG. 4 is a flow sheet schematically illustrating a process for the production of an alkanolamine by the use of a single reactor adapted to recycle the product solution formed therein and deprived partly of ammonia to the reactor.

The second method, as illustrated in FIG. 4, consists in separating and recovering the greater part of ammonia in the ammonia-flashing column and circulating part of the product solution as the alkanolamine containing the remaining ammonia to the reactor.

The second method enjoys a merit of decreasing the amount of circulation, though it entails problems such as enlarging the ammonia-recovering system such as the ammonia-flashing column and further necessitating a booster pump for the circulation.

When it is required to further decrease the amount of the monoalkanolamine formed, the process may be adopted which consists in separating the monoalkanol amine from the alkanolamine after the separation of ammonia in the ammonia-flashing column and circulating the monoalkanolamine to the reactor, though this process increases the expense.

FIG. 3 illustrates a typical flow sheet of the process for producing alkanolamines in the case of recycling part of the product solution to the reactor. In FIG. 3, the reference numerals that result from adding 200 to the reference numerals of FIG. 1 denote the same parts as in FIG. 1 unless otherwise specified. The method illustrated in FIG. 1 can be similarly adopted here excepting that the liquid in circulation is forwarded to the reactor.

Properly, the amount of the product solution to be circulated may be in the range of 5 to 90 vol. %, preferably in the range of 10 to 80 vol. %, and more preferably in the range of 20 to 70 vol. %, based on the total amount of the product solution. If the amount is unduly small, the shortage will be at a disadvantage in not increasing the concentration of the alkylene oxide and consequently failing to acquire dialkanolamines sufficiently. Conversely, if this amount is unduly large, the excess will impair the operation efficiency because the amount of flow volume at the inlet of the reactor is excessively large relative to the amount of production. The term "product solution" as used herein means the product obtained by the reaction of ammonia and an alkylene oxide. The product solution normally contains liquid ammonia and a mixture of a monoalkanolamine, a dialkanolamine, and a trialkanolamine. As examples a mixture emerged from the reactor, with the composition intact after departure from the outlet thereof, and an alkanolamines containing a small amount of ammonia may be cited.

It is preferred in this invention to circulate to the reactor part of the product solution formed in the reactor without thoroughly separating alkanolamine and ammonia therefrom. The reason is that the thorough separation requires the pressure to be adjusted in the range of normal pressure to reduced pressure and incurs an unduly large cost.

The position at which part of the product solution is circulated to the reactor is preferred to be the inlet of the reactor on account of the reaction efficiency.

The alkylene oxide at the inlet of the reactor generally has a concentration in the range of 3 to 35% by weight, preferably in the range of 5 to 30% by weight, and preferably in the range of 8 to 25% by weight, based on the weight of the total raw material. If this concentration is unduly low, the shortage will impair the productivity and proportionately decrease the amount of dialkanolamine. Conversely, if the concentration is unduly high, the reaction can fail to proceed smoothly in an adiabatic reactor since the interior temperature of the reactor is too high to perform the reaction.

FIG. 4 illustrates a typical flow sheet of the process for producing alkanolamines in the case of recycling to the reactor part of the product solution containing a small amount of ammonia after separation of the greater part of ammonia. The monoalkanolamine that has been purified, when necessary, may be recycled. In FIG. 4, the reference numerals that result from adding 100 to the reference numerals of FIG. 3 denote the same parts as in FIG. 3 unless otherwise specified. The method illustrated in FIG. 3 can be similarly adopted here except for the particulars mentioned above.

In this method, the total amount of the product solution equals the amount of the bottom product extracted from the ammonia-flashing column. The amount of circulation indicates the ratio of the amount of the extracted bottom product to be circulated to the reaction system.

Figure 5:
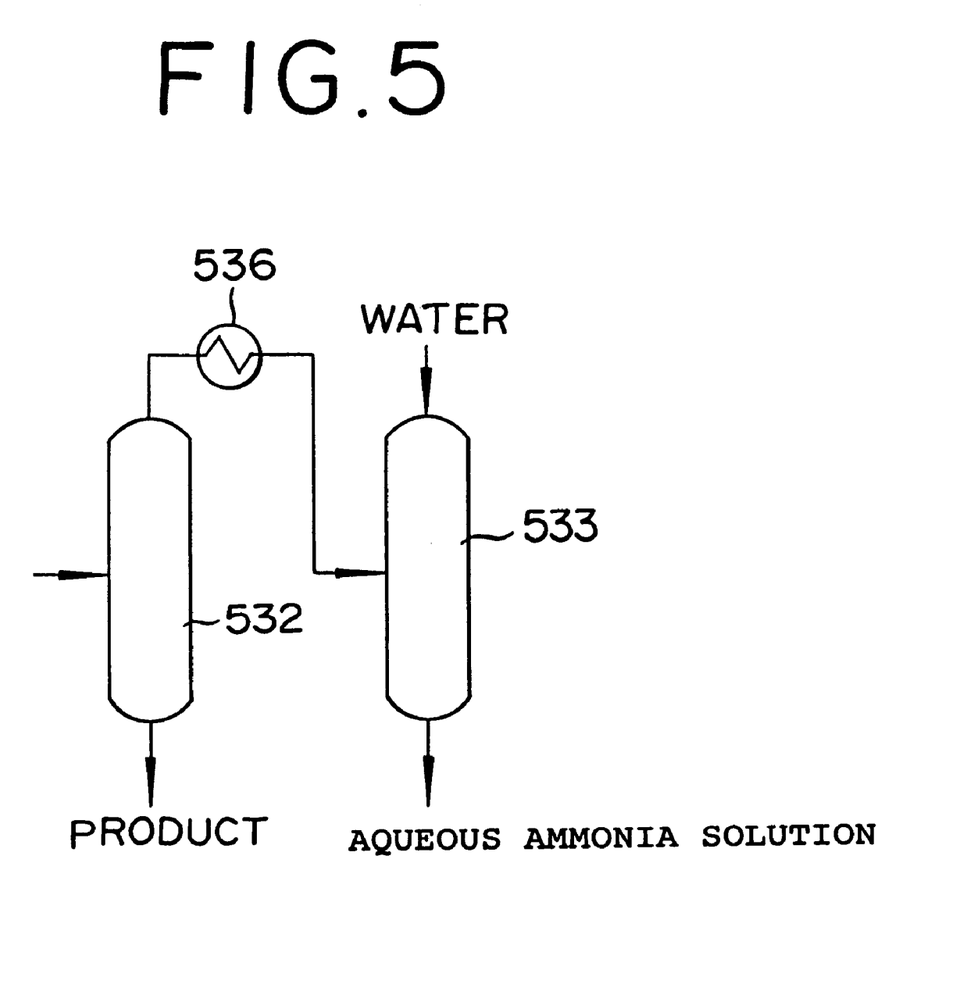
FIG. 5 is a flow sheet illustrating one example of the ammonia-recovering system contemplated by this invention.

FIG. 5 is a flow sheet illustrating the method for recovering, as the aqueous ammonia solution, the ammonia present in the bottom product of the ammonia-recovering column In FIG. 5, the bottom product containing ammonia is supplied to an ammonia-stripping column 532. As the ammonia-stripping column 532, is used a distillation column usually. At this time, it is commendable to add a solution containing water to the bottom product being supplied to the stripping column 532. This solution may contain alkanolamines in addition to water. The ratio of the water may be in the range of 10 to 90 parts by weight, based on 100 parts by weight of the solution. Properly, the amount of the water-containing solution to be added is generally in the range of 10 to 80 parts by weight, preferably in the range of 20 to 70 parts by weight, based on 100 parts by weight of the bottom product. By adding the water-containing solution, it is possible to lower the bottom temperature of the ammonia-stripping column and substantially remove the ammonia in the product. As regards the distillation column, generally the operating pressure is in the range of 50 to 400 kPa and the bottom temperature is in the range of 100° C. to 250° C. The alkanolamine is recovered from the bottom of the ammonia-stripping column 532 and, at the same time, ammonia and water are forwarded through the top of the column to an ammonia-absorption column 533 via a condenser 536. As the ammonia-absorption column 533, a packed column is usually used. As regards the packed column, the operating pressure may be in the range of 50 to 400 kPa and the bottom temperature in the range of 20° C. to 60° C. In the ammonia-absorption column 533, the water is flashed through the top, and the aqueous ammonia solution is recovered through the bottom.

In the method for producing alkanolamines using a solid catalyst, when the unreacted ammonia contained in the product is recovered as liquid ammonia, this liquid ammonia can be reused as the liquid ammonia, i.e. a raw material. This recovery of liquid ammonia generally requires multiple stages of ammonia recovery process. For example, it is possible to liquefy the ammonia by supplying the bottom product containing ammonia to a distillation column of normal pressure, separating ammonia through the top of this column, cooling this ammonia with a condenser that uses brine produced by a refrigerator. At the same time, it obtains the residue through the bottom of the column. The residue thus obtained is supplied to a distillation column of a reduced pressure. Here, a decompressing device is required for the purpose of reducing the pressure using expensive facilities such as refrigerating and decompressing devices. In contrast, this invention can recover ammonia contained in the bottom product as aqueous ammonia solution without the need for expensive equipment such as a refrigerating and a decompressing devices and, thereby is a low cost method. Thus, the method is low cost since incurring these expenses is avoided.

The ammonia in the bottom product is recovered as aqueous ammonia solution. When this method is enabled to attain effective utilization of this aqueous ammonia solution, it constitutes itself a veritably excellent method of recovery.

Now, this invention will be described below by using ethylene oxide as a typical example of the alkylene oxide. This invention is not limited to this example.

In the conventional method for production using aqueous ammonia solution as a raw material (referred to as Method A), it is impossible to repress the formation of triethanolamine while producing diethanolamine copiously. Alternatively, a method has been proposed which employs a catalyst having a high selectivity for the formation of diethanolamine and uses liquid ammonia instead of aqueous ammonia solution (referred to as Method B). When the apparatus for Method A is already possessed and the method of this invention is employed during the establishment of the apparatus for Method B, the aqueous ammonia solution can be advantageously recovered by Method B to be used as a raw material for Method A.

Properly, in this case, the bottom product derived from the ammonia-recovering column of Method B and the water-containing product solution emerged from the reactor of Method A may be mixed and supplied to the ammonia-stripping column of Method A.

Figure 6:
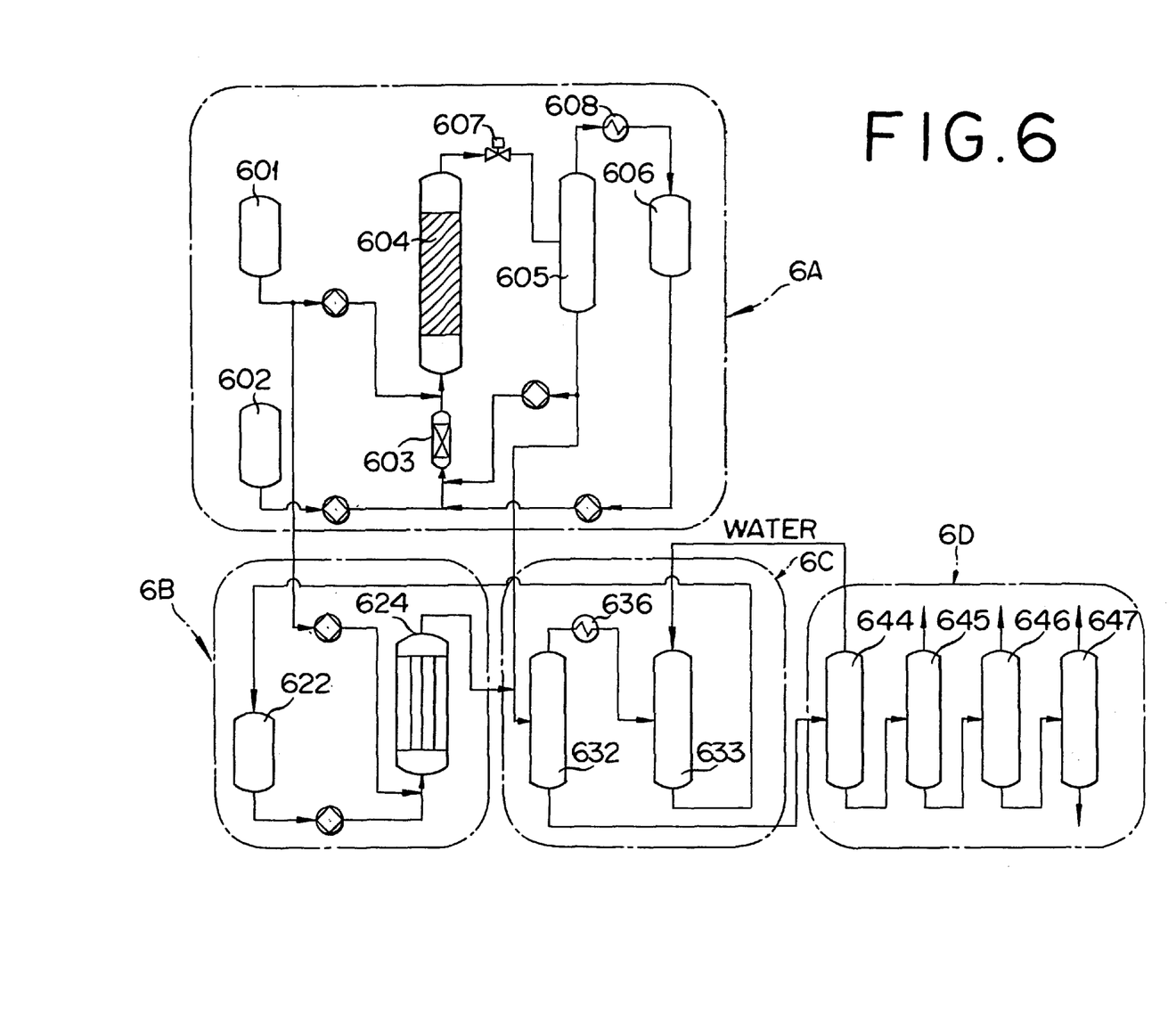
FIG. 6 is a general flow sheet illustrating one example of a process for the production of an alkanolamine according to the invention.

FIG. 6 is a diagram illustrating a typical flow sheet of the method for producing ethanolamines using ethylene oxide (=EO) as the alkylene oxide contemplated by this invention.

The upper block 6A of FIG. 6 illustrates the flow sheet of the method indicated in FIG. 4, the lower left block 6B the conventional process using aqueous ammonia solution as a raw material, the lower central block 6C an ammonia-recovering system, and the lower right block 6D an ethanolamine-purifying system.

From a raw material liquid ammonia tank 602 and are covered liquid ammonia tank 606, is supplied the liquid ammonia via a raw material pre-heater 603 to a reactor 604 by means of a relevant high-pressure pump. On the other hand, EO is supplied from a raw material EO tank 601 to the reactor 604 by means of a relevant high-pressure pump. The reactor 604 may be controlled at a pressure level in the range of 8 to 15 MPa by a pressure-controlling valve 607. The reaction product or liquid emerged from the controlling valve 607 is forwarded to the intermediate stage of an ammonia-recovering column 605 with the inner pressure controlled to a level, e.g., in the range of 1 to 3 MPa. The ammonia that is emerged through the top of the ammonia-recovering column 605 is cooled by a condenser (using ordinary cooling water as the refrigerant) 608 and recovered in a liquid ammonia tank 606. Meanwhile, the bottom product from the ammonia-recovering column 605 contains ethanolamine mixture and 4 to 20% by weight of ammonia. This bottom product is forwarded to an ammonia-stripping column 632 of Method A. Part of this bottom product is circulated to the reactor 604 for the sake of reuse.

The conventional method for producing alkanolamines using aqueous ammonia solution as a raw material can be implemented by the method known to the art. For example, the aqueous ammonia solution from an aqueous ammonia solution tank 622 and the EO from a raw material alkylene oxide tank 601 are forwarded to the reactor 624. The ratio of the ammonia to the EO may be suitably set to suit the purpose of production since the ratio of mono-, di-, and tri-ethanolamines to be obtained varies depending on the ratio of ammonia and EO used. For instance, the ratio of ammonia in the range of 1 to 40 mols, per mol of EO may be cited. The reaction is generally performed in a shell-andtube reactor under a pressure in the range of normal pressure to 16 MPa and a temperature in the range of normal temperature to 150° C. The product solution containing ammonia, water, and ethanolamines is forwarded together with the bottom product from the aforementioned ammonia-recovering column 605 to the intermediate stage of an ammonia-stripping column 632. In the ammonia-stripping column 632, on the one hand through the top are stripped water and ammonia, then which are forwarded to the intermediate stage of an ammonia-absorption column 633, on the other hand from the bottom are recovered water and ethanolamines.

The bottom product from the ammonia-stripping column 632 is forwarded to a dehydrating column 644. The water is expelled through the top of this column 644 and the bottom product thereof is forwarded sequentially to a monoethanolamine (MEA)-purifying column 645, a diethanolamine (DEA)-purifying column 646, and a triethanolamine (TEA)-purifying column 647 to obtain respective products. Incidentally, the components of the ethanolamine mixture are preferably separated using respectively known distillation columns of reduced pressure.

In the layout of FIG. 6, the method illustrated in FIG. 1, FIG. 2, or FIG. 3, respectively, may be employed at Block 6A instead of the method illustrated in FIG. 4.

The third aspect of the invention will be described, which pertains to an apparatus that is used in the production of alkanolamines by the reaction of liquid ammonia and an alkylene oxide in the presence of a solid catalyst. This apparatus is provided with a fixed bed reactor, a pressure-controlling valve disposed on the downstream side of the reactor, a pump for circulating the product solution to the reactor, a booster pump for supplying a raw material ammonia to the reactor, and a booster pump for supplying a raw material alkylene oxide to the reactor. The flow volume in which the product solution formed in the reactor is circulated, is controlled with this circulating pump.

The reactor mentioned above is preferred to be of the adiabatic reactor.

Figure 7:
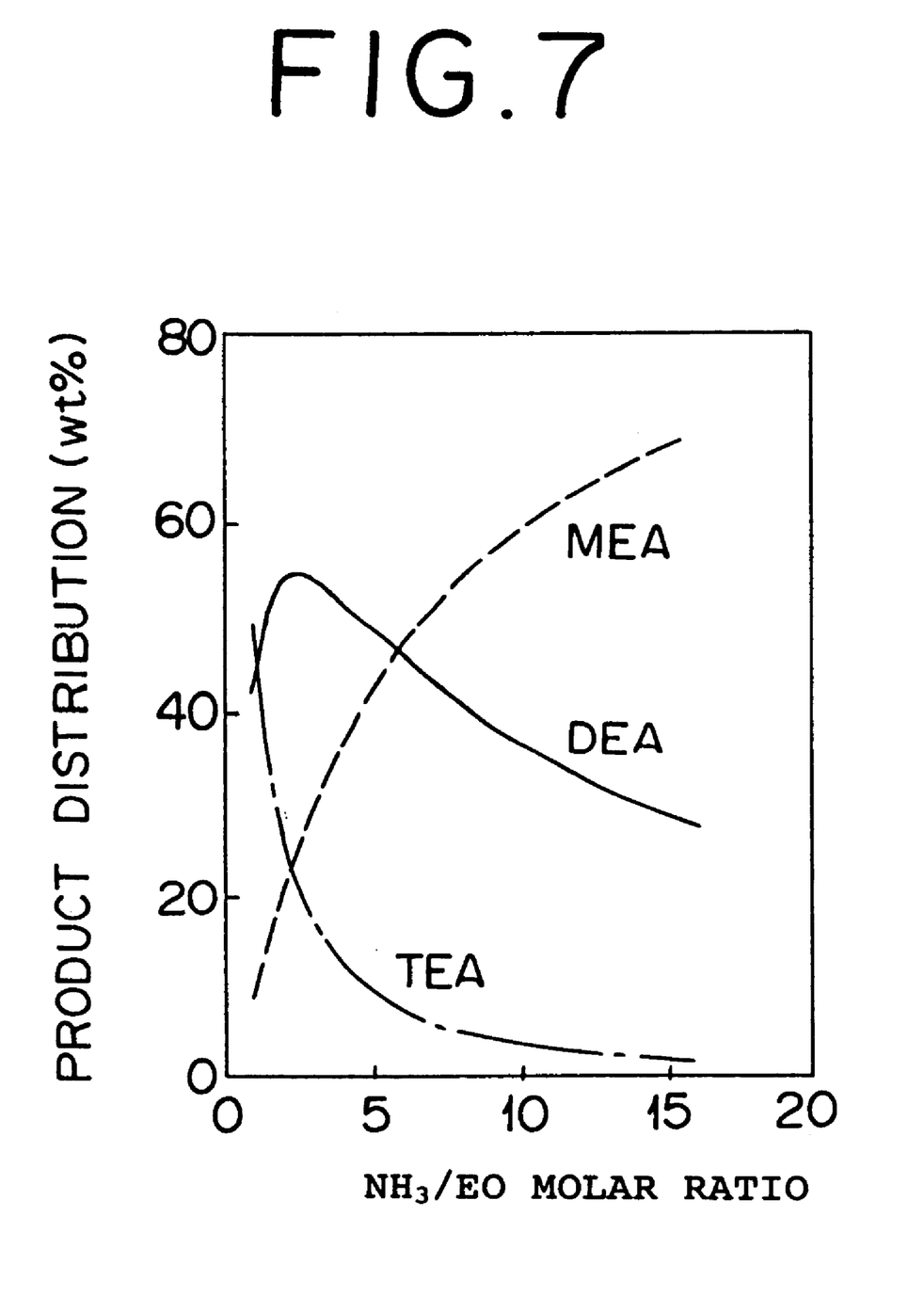
FIG. 7 is a graph showing one example of the change in product distribution due to a change in the molar ratio of ammonia and ethylene oxide.

FIG. 7 is a graph showing one example of the products distribution found in the reaction of ammonia and ethylene oxide performed in the presence of a typical catalyst having a high selectivity for diethanolamine in consequence of variation in the molar ratio of the components. When not less than 50% by weight of diethanolamine, the molar ratio of ammonia/ethylene oxide must be set at a level of not less than 4. The molar ratio attainable by a reactor is approximately not less than 8 in the case of an adiabatic reaction. When the molar ratio is to be set at a level of not more than 4, therefore, the reaction must be performed using not less than two reactors. This invention is highly advantageous for the sake of commercial application because a reactor amply suffices for the execution of the invention.

EXAMPLES

Now, this invention will be described more specifically below with reference to examples. It should be noted, however, that the invention is not limited to these examples.

Example I-1

Ethanolamine was produced as follows, based on the method for producing alkanolamines illustrated in FIG. 6.

A reactor 604 (made of stainless steel and measuring 67 mm in inside diameter and 2 m in length) having an inner volume of 7 L was packed with 6 L of ZSM-5 zeolite beads on which lanthanum had been supported (Si/Al atomic ratio=28, amount of La: 1% by weight, and beads 0.7 to 1.0 mm in diameter).

A tubular pre-heater 603 (200 mm in inside diameter, 1 m in length in the preheating part thereof and containing a packing of 5 mm in diameter) having an electric heater disposed therein was set on the upstream side of the reactor 604. The preheating part was heated with the electric heater.

Then, liquid ammonia and ethanolamine (the simulated liquid of an assumed composition at the outlet of the reactor during the initial stage of the reaction and the bottom product of the ammonia-recovering column 605 in the stationary state) were continuously fed at a fixed rate to the pre-heater 603 using a high-pressure pump. Consequently, the ammonia in the ammonia raw material tank 602 and the EO in the EO raw material tank 601 were mixed and heated and the mixture consequently formed was supplied to the reactor 604. The reactor 604 was retained in a substantially adiabatic state by being slightly heated with a heater (electric heater) not shown for replenishing such an amount of heat as was lost through radiation. The reaction pressure was controlled at 12 Mpa. Then, the EO and ammonia were allowed to react continuously. The inlet temperature was controlled at 40° C. and the reaction pressure at a fixed level of 10 MPa with a controlling valve at the outlet of the reactor. The temperature of the catalyst bed at the outlet of the reactor had been settled at 150° C. The reactor 604 was provided at the outlet thereof with an ammonia-recovering column 605, which was operated under a pressure of 2 MPa to separate the greater part of ammonia and store it in a container 606.

As regards the flow volumes of raw materials in the stationary state, the bottom product from the ammonia-recovering column 605 was fed at a rate of 3.14 kg/hr, the recycled ammonia and the freshly supplied ammonia were fed at a total rate of 6.4 kg/hr, and the EO was fed at a rate of 2.36 kg/hr to the reactor 604. The ethanolamine composition, MEA/DEA/TEA, of the product solution was 32.9/56.7/10.5 by weight ratio.

The bottom product from the ammonia-recovering column 605 was fed to an ammonia-stripping column 632 at the same ratio of 3.14 kg/hr as the volume of circulation. The bottom product had an ammonia content of 7 wt. %. In the column 605, 93% of the ammonia in the product solution was recovered as liquid ammonia and stored in a tank 606.

To the column 632, was fed the product solution produced by the conventional method using aqueous ammonia solution as a raw material in conjunction with the bottom product mentioned above. Here, a solution composed of MEA/DEA/TEA/NH$_3$/H$_2$O at a weight ratio of 12/11/8/23/46 was fed as a simulated liquid at a ratio of 3.55 kg/hr. The column 632 was operated under a pressure of 0.2 MPa at a bottom temperature of 150° C. to strip water and ammonia through the top thereof. The bottom product was composed of MEA/DEA/TEA/H$_2$O at a weight ratio of 30/40/14/16. The water and ammonia that were stripped through the top of the column were cooled with cooling water and then introduced into the ammonia-absorption column 633. This column 633 was operated to recover ammonia as aqueous ammonia solution under a pressure of 0.2 MPa at a bottom temperature of 40° C., with the feed rate of water through the top fixed at 0.5 kg/hr. This aqueous ammonia solution was used as a raw material for the conventional aqueous ammonia solution process.

In the method for producing alkanolamines using liquid ammonia as a raw material, the aqueous ammonia solution recovered could be effectively utilized in Method A.

Example I-2

The procedure of Example I-1 was repeated, except that the system for the reaction illustrated in Block 6A was changed to a system provided with a plurality of reactors as illustrated in FIG. 2. In the actual operation, the reaction was performed not with three reactors but with a reactor that was modulated as three reactors. The catalyst and the reactor used herein were the same as those of Example I-1. The product solution was not recycled. The temperatures and the pressures of the other reactors were the same as that of Example I-1.

First reactor: As respects the flow volumes of raw materials, the recycled ammonia and the freshly supplied ammonia were fed to the reactor at a total rate of 8 kg/hr and the EO was fed at a rate of 2 kg/hr. The ethanolamine composition, MEA/DEA/TEA, of the product solution was 61.5/37.0/1.5 by weight ratio.

Second reactor: EO was added to the product solution of the first reactor. A modulated liquid having ethanolamine incorporated in the same composition as the outlet composition of the first reactor was prepared. The recycled ammonia and the freshly supplied ammonia were fed to the reactor at a total rate of 7.4 kg/hr, the EO was fed at a rate of 2 kg/hr, and ethanolamine was fed at a rate of 2.6 kg/hr. The ethanolamine composition, MEA/DEA/TEA, of this product solution was 44.2/51.8/4.0 in weight ratio.

Third reactor: EO was added to the product solution of the second reactor. A modulated liquid having ethanolamine incorporated in the same composition as the outlet composition of the second reactor was prepared. The recycled ammonia and the freshly supplied ammonia were fed to the reactor at a total rate of 6.93 kg/hr, the EO was fed at a rate of 2 kg/hr, and ethanolamine was fed at a rate of 5.1 kg/hr to the reactor. The ethanolamine composition, MEA/DEA/TEA, of this product solution was 33.8/59.4/6.8 in weight ratio.

The bottom product from the ammonia-recovering column 605 was fed at a rate of 7.48 kg/hr to the ammonia-stripping column 632. The bottom product had an ammonia content of 7.1 wt. %. In the column 605, was recovered 91% of the ammonia in the product solution.

To the column 632, was also fed the product solution produced by the conventional method and used for the purpose of mixture. Here, a solution composed of MEA/DEA/TEA/NH$_3$/H$_2$O at a weight ratio of 12/11/8/23/46 was fed as a simulated liquid at a rate of 9.58 kg/hr to the column 632. The column 632 was operated under a pressure of 0.2 MPa at a bottom temperature of 150° C. to strip water and ammonia through the top thereof. The bottom product was composed of MEA/DEA/TEA/H$_2$O at a weight ratio of 35.6/38.8/9.6/16. The water and the ammonia that had been stripped through the top of the column 632 were cooled with cooling water and introduced into the ammonia-absorption column 633. This column 632 was operated to recover ammonia as aqueous ammonia solution under a pressure of 0.2 MPa at a bottom temperature of 40° C., with the feed rate of water through the top of the column fixed at 1.5 kg/hr. This aqueous ammonia solution was used as a raw material for the conventional method.

Example II-1

Figure 8:
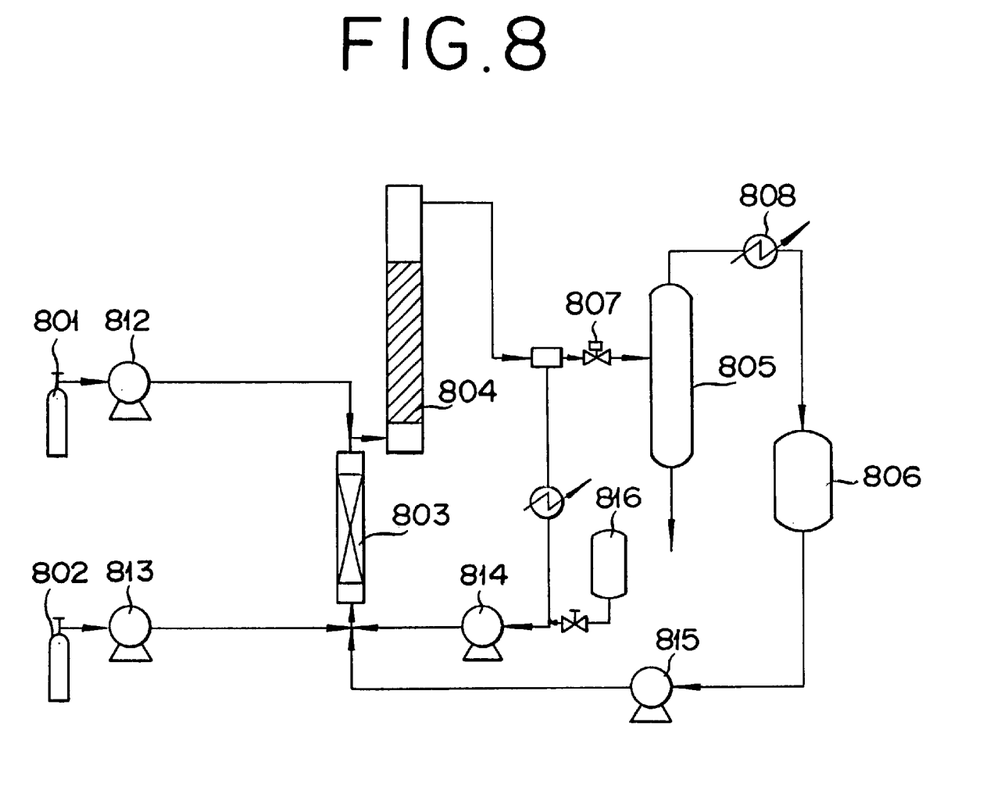
FIG. 8 is a flow sheet of the reaction apparatus used in the present example.

FIG. 8 is a flow sheet illustrating one mode of embodying the method for production of an alkanolamine according to this invention. This reaction was performed using an apparatus illustrated in FIG. 8. Specifically, an insulating heater (not shown) was helically wound around the exterior of a reactor 804 that was made of a stainless steel tube measuring 20 mm in inside diameter and 200 mm in length. A heater wound was helically around the exterior of a pre-heater 803 that was made of a stainless steel tube measuring 10 mm in inside diameter and 100 mm in length. The catalyst bed was formed by packing 40 cm$^3$ of a catalyst obtained by compression molding ZSM-5 zeolite that had been ion-exchanged with lanthanum and then crushing the produced molded particles to a particle size in the range of 50 to 100 mesh. The β value was found to be 0.13.

A simulated liquid of 64% by weight of ammonia, 17% by weight of monoetanolamine, and 19% by weight of diethanolamine for the initial stage of the reaction was introduced as the circulation liquid into a tank 816. The circulating liquid was forwarded at a rate of 86 g/hr with a pump 814 and the ethylene oxide from an ethylene oxide tank 801 was forwarded at a rate of 13.2 g/hr with the pump 812 to the reactor 804. In the reactor 804, the inlet temperature was fixed at 60° C. and the internal pressure at 12 MPa with a controlling valve 807 disposed at the outlet of the reactor. At the outlet of the reactor, the temperature of the catalyst bed was settled at 150° C. The reactor was provided at the outlet thereof with an ammonia-flushing column 805, which separated the greater part of ammonia, forwarded it via a heat exchanger 808, and stored it in a container 806.

After the reaction was stabilized, it was continued using the product solution instead of the simulated liquid. Specifically, the product solution was fed at a rate of 50 g/hr, the circulated ammonia and the freshly supplied ammonia were fed at a total rate of 34.2 g/hr, and ethylene oxide was fed at a rate of 15.3 g/hr to the reactor 804. At this time, the freshly supplied ammonia was supplied from the ammonia tank 802 to the reactor 804 via the pump 813. The reaction was performed for one day to confirm that the reaction was stabilized in the meantime. This product solution was composed of monoethanolamine (MEA), diethanolamine (DEA), and triethanolamine (TEA) at a weight ratio of 41.6/51.7/6.7.

At this time, the flow rate of the product solution at the outlet of the reactor 804 was 100 g/hr and the amount of circulation was 50 vol. % of the product solution and the ethylene oxide concentration in the raw materials was 15.3% by weight.

The distribution of the products consequently obtained was shown in Table 1.

Examples II-2 to II-4

The procedure of Example II-1 was repeated, except that ratios of the circulating liquid to the product solution produced and the ethylene oxide concentration in the raw materials for reaction were changed, respectively.

These distributions of the products consequently obtained were shown in Table 1.

Example II-5

The procedure of Example II-1 was repeated, except that a catalyst bed was formed by packing 40 cm$^3$ of a catalyst obtained by compression molding ZSM-11 zeolite that had been ion-exchanged with yttrium and then crushing the produced molded particles to a particle size in the range of 50 to 100 mesh, the simulated liquid was changed to of 47% by weight of monoethanolamine and 53% by weight of diethanolamine, and the flow volume was changed to 31 g/hr.

After the reaction was stabilized, the supply from the simulated liquid tank 816 was stopped, and 50% by weight of the bottom product from the ammonia-flushing column 805 was circulated to the inlet of the reactor 804. The reaction was performed for one day with the flow rate of ammonia adjusted so as to control the ethylene oxide concentration in the raw materials to 15.3% by weight, to confirm that the reaction was stabilized in the meantime. The ethanolamine composition, MEA/DEA/TEA, of the product solution had a weight ratio of 41.6/51.7/6.7.

Comparative Example II-1

The procedure of Example II-1 was repeated, except that the circulation of the product solution was omitted and the flow rate that of ammonia was changed to 84.4 g/hr and that of ethylene oxide to 15.6 g/hr. The distribution of the products consequently obtained is shown in Table 1.

Comparative Example II-2
(Monoethanolamine Used as the Circulating Liquid)

The procedure of Example II-1 was repeated, except that a catalyst 60 cm$^3$ of molded particles of the montmorillonite (0.5 mm in diameter and 2 to 5 mm in length; the β value was 1.06) that had been ion-exchanged with lanthanum was used and monoethanolamine isolated from the produced ethanolamine was used as the circulating liquid.

The reaction was carried out with the same catalyst in the same reactor as above while using ammonia, monoethanolamine, and ethylene oxide as raw materials at a weight ratio of 66/18/16. The total flow volume of the product solution was 100 g/hr.

The net product composition, MEA/DEA/TEA, minus the MEA used for the circulation had a weight ratio of 53.1/41.0/5.9. Thus, the DEA could be obtained in a slightly larger amount and the TEA could be formed in a suppressed proportion. The proportion 62% of the MEA, however, might be purified from the ethanolamine present in the outlet product solution prior to use as the raw material. This purification incurred a very large expense of utility and increased the cost of equipment for the purification of monoethenaolamine to 2.6 times the normal level.

Comparative Example II-3
(Product Solution Used as the Circulating Liquid)

The procedure of Example II-1 was repeated, except that a catalyst 60 cm$^3$ of molded particles of the montmorillonite (0.5 mm in diameter and 2 to 5 mm in length; the value was 1.06) that had been ion-exchanged with lanthanum.

During the period of stationary phase, the operation was performed under the conditions setting the total feed rate of the recycled ammonia and the freshly supplied ammonia at 34.1 g/hr and the feed rate of ethylene oxide at 15.9 g/hr and the circulating volume of the product solution at 50 g/hr.

At this time, the ethanolamine composition, MEA/DEA/TEA, in the product solution had a weight ratio of 60.2/26.6/13.2, indicating that the proportion of DEA was small and the proportion of TEA was as much as 50% of that of DEA.

The reaction for converting DEA to TEA was liable to occur since the β value of this catalyst was as large as 1.06. When the circulating liquid contained DEA, this DEA was gradually transformed into TEA.

When the product solution was used as the circulating liquid, the selectivity for DEA was low by as much as 14%, the selectivity for TEA was high by as much as 7%, and the amount of DEA formed was small as compared with the case of using MEA as the circulating liquid as demonstrated in Comparative Example 2.

TABLE 1

|  | Ratio of circulating liquid (wt %) | EO concentration (wt %) | Distribution of products (wt %) | | |
|---|---|---|---|---|---|
|  |  |  | MEA | BEA | TEA |
| Example II-1 | 50 | 15.3 | 41.6 | 51.7 | 6.7 |
| Example II-2 | 50 | 11.1 | 51.6 | 44.4 | 3.9 |
| Example II-3 | 40 | 16.1 | 31.0 | 57.2 | 11.8 |
| Example II-4 | 33 | 18.5 | 18.7 | 58.4 | 22.9 |
| Comparative Example II-1 | 0 | 15.6 | 68.5 | 30.6 | 0.9 |

MEA: Monoethanolamine
DEA: Diethanolamine
TEA: Triethanolamine
EO: Ethylene oxide Comparison of the data of Example II-1–II-4 with those of Comparative Example II-1 shown in Table 1 reveals that by circulating the product solution, it was possible to obtain diethanolamine in a larger amount by one stage of reaction.

The entire disclosure of Japanese Patent Application Nos. 2000-385145, 2001-297495, and 2001-297496 filed on Dec. 19, 2000, Sep. 27, 2001, and Sep. 27, 2001 including specification, claims, drawings and summary are incorporated herein by reference in its entirety.

What is claimed is:

1. A method for producing alkanolamines, which comprises:

producing a product solution from liquid ammonia and an alkylene oxide using a solid catalyst in a reactor, wherein said solution comprises alkanolamines and unreacted ammonia;

forwarding the product solution to an ammonia-recovering column disposed downstream of the reactor;

recovering not less than 60% by weight of the unreacted ammonia, based on the weight of the product solution exiting from the outlet of the reactor, as liquid ammonia and a bottom product of the ammonia-recovering column;

directing the bottom product to an ammonia-stripping column in which the ammonia is stripped out;

leading the stripped ammonia to an ammonia absorption column in which the ammonia is absorbed by means of water, thereby recovering it as an aqueous ammonia solution.

2. A method according to claim 1, wherein a molar ratio of the ammonia to the alkylene oxide is in the range of 2 to 30:1.

3. A method according to claim 1, wherein a reaction temperature for producing the alkanolamines is in the range of 20° C. to 200° C.

4. A method according to claim 1, wherein a ratio, β ($k_3/k_2$), is not more than 0.7, wherein the $k_2$ representing the rate constant of the reaction of monoalkanolamine and an alkylene oxide and the $k_3$ representing the rate constant of the reaction of dialkanolamine and an alkylene oxide, by the use of the catalyst.

5. A method according to claim 1, wherein the catalyst is a microporous material having an effective pore diameter in the range of from 0.45 nm to 0.8 nm.

6. A method according to claim 5, wherein the microporous material is ion-exchanged with a rare earth metal and/or surface-treated.

7. A method according to claim 1 further comprising adding a water-containing solution to the bottom product that is being directly supplied to the ammonia-stripping column.

8. A method according to claim 7, wherein the water-containing solution includes an alkanolamine.

9. A method according to claim 1 further comprising circulating part of the product solution to the inlet of the reactor.

10. A method according to claim 1, wherein the recovered aqueous ammonia solution is fed as a raw material to an apparatus for the production of alkanolamines by the aqueous ammonia solution method.

11. A method for producing alkanolamines by the reaction of liquid ammonia and a corresponding alkylene oxide using a solid catalyst, said method comprising:
   circulating part of a product solution to the reactor, wherein the product solution comprises a mixture of alkanolamines and ammonia.

12. A method according to claim 11, wherein a molar ratio of the ammonia to the alkylene oxide is in the range of 2 to 30:1.

13. A method according to claim 11, wherein a reaction temperature for producing the alkanolamines is in the range of 20° C. to 200° C.

14. A method according to claim 11, wherein an amount of the product solution circulated to the reactor is in the range of 5 to 90 vol. % of the total amount of the product solution.

15. A method according to claim 11, wherein an alkylene oxide concentration at the inlet of the reactor is in the range of 3 to 35% by weight.

16. A method according to claim 11 wherein the reaction has a ratio, $\beta$, of not more than 0.7.

17. A method according to claim 11, wherein the catalyst is a microporous material having an effective pore diameter in the range of from 0.45 nm to 0.8 nm.

18. A method according to claim 17, wherein the microporous material is ion-exchanged with a rare earth metal and/or surface-treated.

19. A method according to claim 10, further comprising:
   mixing the bottom product with a reactive liquid produced by an aqueous ammonia solution method for production of alkanolamines; and
   feeding the mixture to an ammonia-stripping column in the aqueous ammonia solution method.

20. A method according to claim 10, wherein an amount of ammonia contained in the bottom product is 4 to 20% by weight, such that the amount is less than the amount of raw material ammonia to be used in the aqueous ammonia solution method.

* * * * *